United States Patent [19]

Wells

[11] 4,257,746
[45] Mar. 24, 1981

[54] DOSIMETER HAVING A LOW AIR FLOW RATE

[75] Inventor: Adoniram J. Wells, Wilmington, Del.

[73] Assignee: E. I. Du Pont de Nemours and Company, Wilmington, Del.

[21] Appl. No.: 948,037

[22] Filed: Oct. 2, 1978

[51] Int. Cl.³ .............................................. F04B 49/00
[52] U.S. Cl. ........................................ 417/43; 417/45; 417/63
[58] Field of Search .................................. 417/42–44, 417/63, 45, 413, 12; 73/211, 28, 30

[56] References Cited

U.S. PATENT DOCUMENTS

| | | | |
|---|---|---|---|
| 3,198,121 | 8/1965 | Schaub | 417/43 X |
| 3,406,895 | 10/1968 | Bauer et al. | 417/309 X |
| 3,410,059 | 11/1968 | Garnier | 417/413 X |
| 3,501,899 | 3/1970 | Allen | 417/43 X |
| 3,953,152 | 4/1976 | Sipin | 417/45 |
| 4,063,824 | 12/1977 | Baker et al. | 417/63 X |
| 4,123,932 | 11/1978 | Baker et al. | 73/28 |

Primary Examiner—Carlton R. Croyle
Assistant Examiner—Edward Look

[57] ABSTRACT

An improved dosimeter having a low air flow rate for monitoring working areas in which air is pumped through the dosimeter at a controlled constant low rate of flow and any particles or vapors in the air are collected on a filter, a variable drive pump having an inlet and an outlet is connected to the filter and is driven by an electric motor and controlled by a feed back circuit of an integrator and an amplifier and the pump maintains a constant flow of air through the dosimeter; in operation of the dosimeter the integrator receives a signal from a pressure switch that detects changes in the flow of the air stream through the dosimeter by a change in a pressure drop of the air which is being pumped through an orifice;

The improvement is the use of an adjustable by-pass valve connected in parallel with the variable drive pump in such a manner that regulated quantities of air from the outlet of the pump are recycled to the inlet of the pump thereby allowing the pump to provide a constant low flow rate of air;

In utilization of the dosimeter, the dosimeter is placed in a work area or worn by an individual and at the termination of a period of time, such as a work day, the filter is removed and the contents collected are analyzed by conventional techniques such as gas chromatography to determine a level of exposure of individuals working in that area.

16 Claims, 3 Drawing Figures

DOSIMETER HAVING A LOW AIR FLOW RATE

BACKGROUND OF THE INVENTION

Field of the Invention

This invention relates to a dosimeter for monitoring workers and working areas and in particular a dosimeter having a low air flow rate.

Dosimeters are known and have been used in effort to determine the level of exposure of workers to foreign substances in air, for example, to chemical vapors or fumes, dust particles and the like. A dosimeter is placed in a work area or worn by an individual and air is pumped through a filter which traps foreign substances in the air. At the end of an exposure period, the filter is removed and analyzed for any foreign substances. Such dosimeters are shown in U.S. Pat. No. 4,063,824 issued Dec. 20, 1977 to Baker and Clark and U.S. Ser. No. 800,430 filed May 25, 1977.

One problem with such dosimeters is that a dosimeter designed to utilize a high flow rate of air such as 500–4000 cubic centimeter per minute (cc/min.) cannot be operated at a low flow rate such as 25–125 cc/min. Internal friction of the pump in the dosimeter when operated at low speeds to provide low air flow rates causes the pump to operate irregularly. High air flow rates are desired for dosimeters that use filters to measure dust particles in the air. Low air flow rates are desired for dosimeters that use filters such as charcoal filters to measure vapors or fumes in the air. Dosimeters containing pumps designed to operate at low air flow rates cannot be operated at high air flow rates.

Instead of having several dosimeters that operate at different air flow rates, there is a need for a single dosimeter designed in such a manner that both high and low air flow rates are provided and wherein the air flow rates are accurate, uniform and controlled.

SUMMARY OF THE INVENTION

An improved dosimeter having a low air flow rate for monitoring working areas or individuals has a filter means in which particles or vapors in an air stream pumped through the dosimeter are collected on the filter means, an electric motor, a power source, an exhaust port, a variable drive pump, having an inlet and an outlet and tubularly connected to the filter means and coupled to the electric motor, draws the air stream through the filter means;

an orifice positioned in a tube attached to the pump and to the exhaust port wherein the air stream is pumped through the orifice by the pump and thereby creates an air pressure drop which varies with the flow of the air stream;

a means for reducing pulsations in the air stream;

a differential pressure switch positioned in a tube connected in effect parallel to the orifice and is activated by a change in the air pressure drop of the air stream and creates a low voltage electrical input signal;

an integrator circuit electrically connected to the power source and to the pressure switch uses the low voltage input signal generated by the pressure switch and integrates this signal; and an amplifier circuit electrically connected to the power source and connected in series to the integrator circuit and to the electric motor which amplifies the signal generated by the integrator circuit and feeds this amplified signal to the electric motor, thereby controlling the speed of the motor driving the pump in relationship to the signal generated by the pressure switch, to maintain the air stream at a controlled constant flow rate;

the improvement that is used therewith to provide a constant low air flow rate of the air stream through the dosimeter comprises an adjustable by-pass valve connected in parallel with the variable drive pump such that regulated quantities of air from the outlet of the pump are recycled to the inlet of the pump thereby allowing the pump to provide a constant low flow rate of air.

In utilization of the dosimeter, the dosimeter can be placed in a work area or worn by an individual to monitor the environment to which the worker is exposed. After the dosimeter is placed into operation usually for a given period of time such as an 8 hour shift, the filter is removed from the dosimeter and the contents of the filter are analyzed to determine the substances and amounts of these substances to which a worker was exposed in the period of time. The adjustable by-pass valve of the improved dosimeter allows the dosimeter to be operated at a high air flow rate recommended for the collection of dust particles and at a low air flow rate recommended for vapors or fumes.

Figure 1:
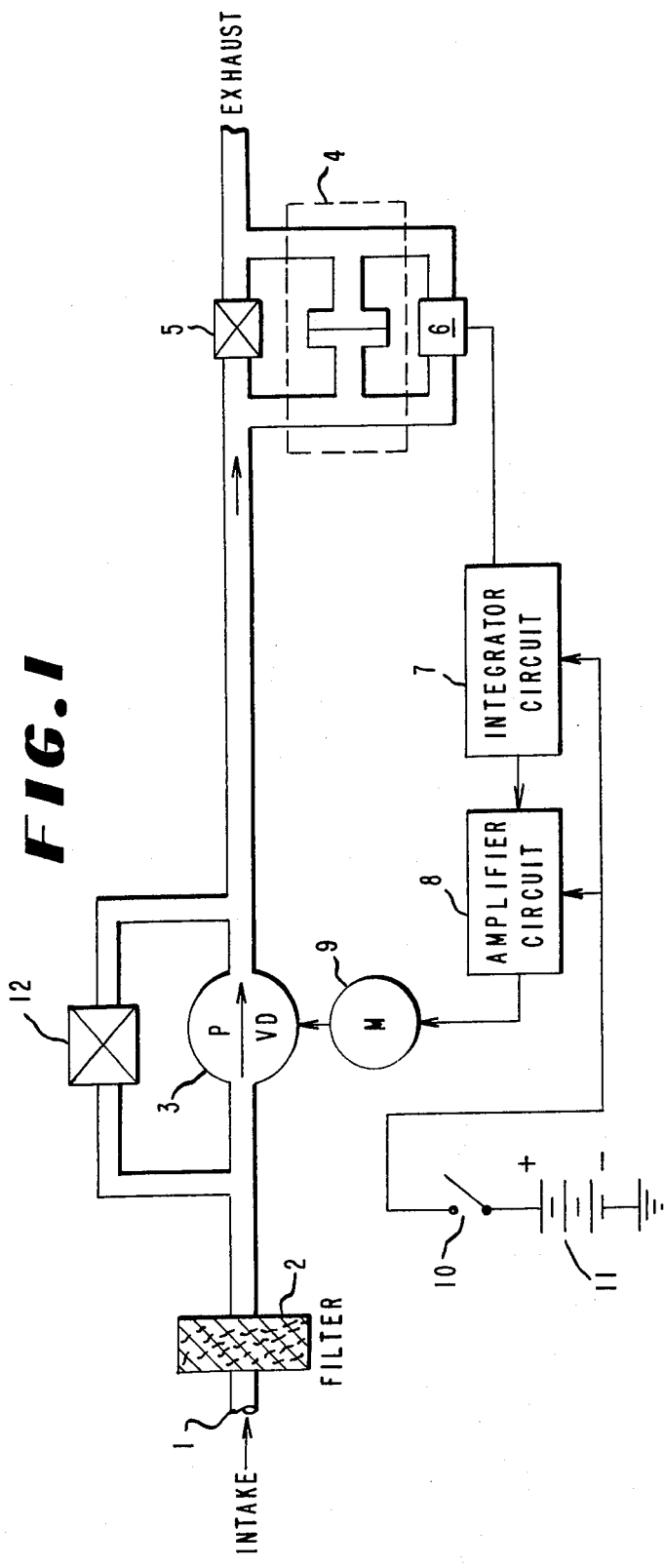
FIG. 1—is a diagram of the dosimeter.

Referring to the diagram of FIG. 1, a basic arrangement of the area dosimeter is shown. Air is pumped in at the intake 1 at a constant flow rate and passed through a filter 2. The air intake and filter are connected by a tube to a variable drive air pump 3 having an inlet and outlet driven by an electric D.C. motor 9. An adjustable by-pass valve 12 is connected in parallel with the pump 3 so that regulated quantities of air from the outlet of the pump can be recycled to the inlet of the pump which allows the pump to provide a constant low flow rate of air. Air at a low flow rate is pumped through an orifice 5 positioned in tube leading to the exhaust port that causes an air pressure drop. One means for reducing pulsations in the air stream is the use of a differential pulsation filter 4 which is positioned in a tube connected to the exhaust port and in parallel with the orifice 5. A pressure switch 6 is positioned in parallel to the differential pulsation filter and is activated by any change in the air pressure drop. The pressure switch 6 is electrically connected to the integrator circuit 7 which utilizes the input from the pressure switch and generates an electrical signal. The signal generated by the integrator 7 is fed to the amplifier circuit 8 which amplifies the signal and the signal controls the speed of the electric motor 9 driving the pump 3 to provide a controlled constant flow rate of air through the dosimeter. The integrator and the amplifier are electrically connected to a D.C. power source 11 which usually is a battery. An on-off switch 10 is positioned between the power source 11 and the amplifier and integrator circuits.

Configuration other than the above for the dosimeter can be used. For example, the orifice can be tubularly connected in series to the filter and the pump. The pump draws an air stream through the orifice and through the filter. As above, a pulsation filter and a pressure switch are in parallel relationship to the orifice and the switch measures any change in an air pressure drop. In another example, a filter and orifice are tubularly connected in series to a pump and the pump draws the air through the filter and orifice. A pulsation filter and a pressure switch are positioned in parallel to the orifice and the switch measures any change in an air pressure drop. In any of the above configurations, the dosimeter would operate without the pulsation filter but the life of the pressure switch would be substantially shortened. Also, in any of the above configurations, the flow rate of the air stream is determined by setting of the adjustable by-pass valve, the size of the opening in the orifice and the pressure required to activate the pressure switch.

The filter 2 of the dosimeter can be adapted to entrap almost any type of substance such as gases, liquids or solids. If mechanical filtration is only required, for example, to collect dust particles to which a worker is exposed, a filter is provided which will entrap particles of 0.01 microns or larger. If the filter is to entrap a gas such as sulfur dioxide, a chemical filter is used which will entrap this gas. If vapors are to be entrapped, then a filter such as a charcoal filter, is used which entraps vapors. At the end of a period, such as an 8-hour shift, during which the dosimeter is in use monitoring an area, the filter is removed and examined for the substance or substances which were present in the work area. A simple count of particles under a microscope may be used or the filter can be analyzed, for example, with a gas chromatograph or for weight increase by a gavimetric analyzer.

A variable drive air pump is used in the dosimeter. A multicylinder air pump such as a four cyclinder diaphragm pump can be used that pumps air from about 500 to 10,000 cubic centimeters per minute (cc/min.) at a continuous flow. The pump is electrically connected to a conventional D.C. motor of about 0.0001–0.1 horsepower. The motor is a variable speed motor and operates from about 5 to 10,000 revolutions per minute. (r.p.m.) However, at a lower r.p.m. the pump binds, seizes and stops and starts and in general pumps irregularly. Therefore, it is desirable to operate the pump at about 200 to 1200 r.p.m. for continuous and smooth operation. To achieve air flow rates below 500 cc/min. the adjustable by-pass valve 12 is used and air flow rates of about 1–500 cc/min. can readily be achieved with uniform operation of the pump.

A single cylinder variable drive diaphragm pump also can be used that pumps air from about 10–3000 cc/min. Usually, an air reservoir position between the pump and the orifice 5 is used as a means for reducing pulsations in the air stream with this single cylinder type of pump. The air reservoir is used instead of the differential pulsation filter. A dosimeter having such as reservoir is shown in the aforementioned U.S. Pat. No. 4,063,824. To attain air flow rates below 10 cc/min. with such a dosimeter, an adjustable by-pass valve is used.

Other pumps such as piston pumps, rotary pumps or centrifugal pumps can also be used.

By opening the adjustable by-pass valve 12, air is recycled from the outlet to the inlet of the pump which lowers the air flow rate through the dosimeter. By closing the by-pass valve, the air flow rate through the dosimeter is increased. Proper adjustment of the by-pass valve will achieve the desired air flow rate through the dosimeter.

The by-pass valve can be an adjustable needle valve or a valve with a fixed opening or instead of a valve, a fixed orifice can be used with or without a shut off valve. Two valves in series can be used; one valve is used for a coarse adjustment and the other for a fine adjustment.

Usually a belt is used to connect the motor to the pump. By using an arrangement of pulleys of different sizes, the speed of the motor can be changed. An advantage of a belt and pulleys is that the belt will slip if the pump becomes restricted and no damage to the motor will result. The motor can also be connected directly to the pump or connected by gears to the pump.

An orifice is positioned in a tube connecting the pump to the exhaust port. The orifice creates a pressure drop in the air stream of about 0.3–10 inches of water. Usually a pressure drop of about 3 inches of water is used and correspondingly, a pressure switch with a set point of 3 inches of water is used therewith. A fixed or an adjustable orifice can be used. Examples of fixed orifices are a venturi tube and a plate with a hole of the desired size. A typical adjustable orifice which preferably is used is an adjustable needle valve. Preferably, an adjustable dual tapered needle valve is used that provides a coarse adjustment and then a fine adjustment to accurately provide a desired pressure drop.

The differential pulsation filter eliminates pressure surges in the air stream caused by the pump so that the pressure switch does not operate on each pressure surge generated by each pump stroke but operates on the average pressure drop across the orifice thereby extending the life of the pressure switch. The pulsation filter also causes a delay of the pressure signal traveling to the pressure switch. This delay is caused by the circuitry controlling the pump to increase the speed or slow the speed of the pump in a repeatable manner.

Figure 2:
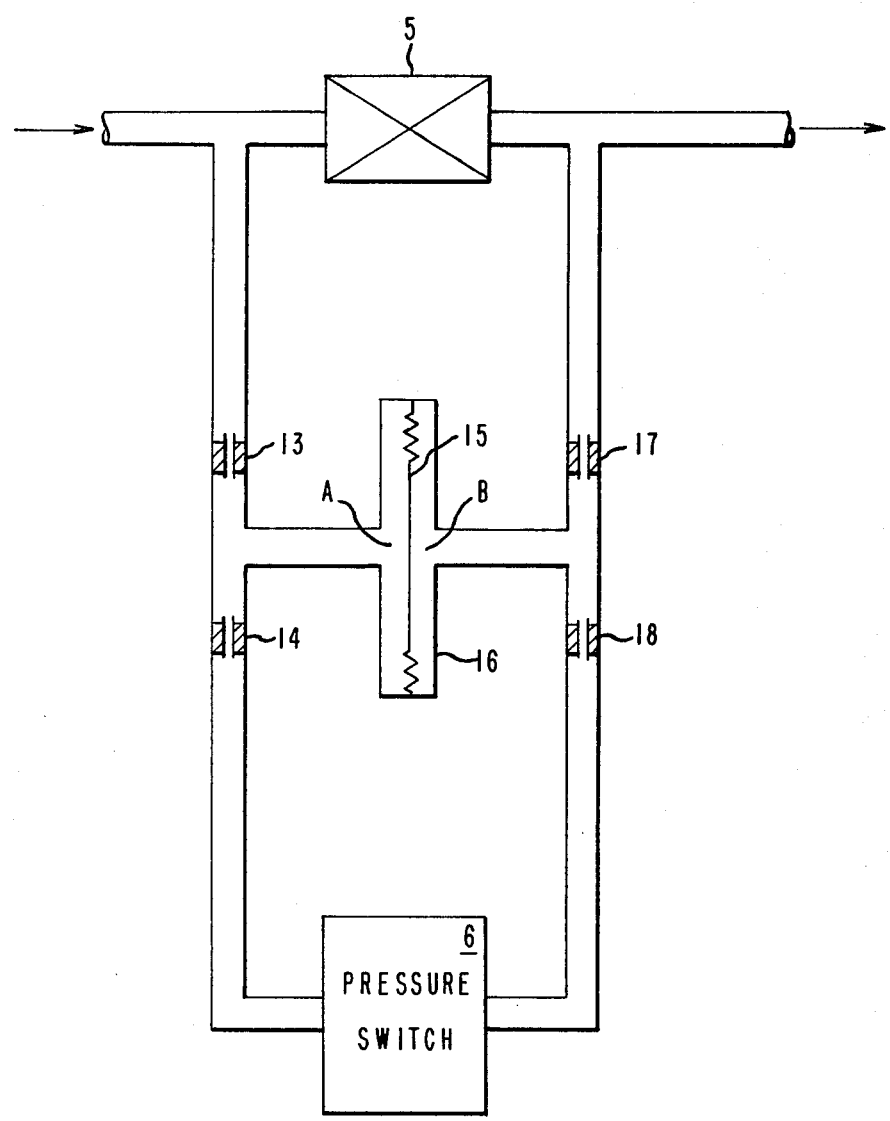
FIG. 2—is a diagram of the differential pulsation filter.

FIG. 2 shows the elements of the differential pulsation filter. The air from the pump flows through the orifice 5. A pressure drop across the orifice 5 is created which generates a higher pressure on the inlet than on the exhaust side of the orifice 5. The higher pressure is transmitted to the pressure switch through orifices 13 and 14 which reduce surges in the air stream. A pressure surge in the air stream on the inlet side of the orifice 5 first passes through 13 and fills the A compartment of the accumulator chamber 16. In this chamber, a flexible diaphragm 15 allows considerable volume change before sufficient pressure builds up and forces the flow of air through orifice 5. The surge coming into compartment A causes the diaphragm 15 to move which in turn generates a pressure pulse in compartment B, or the other side of the diaphragm 15 and starts this smaller pulse flowing through orifice 18 to the low side of the pressure switch 6. This action substantially reduces the surge on the high pressure side of pressure switch 6 which has been further moderated by orifice 14. The exhaust side of the orifice 5 must be connected to the low side of the pressure switch so that the pressure switch 6 can operate in a differential mode. The connection to the low pressure side of the pressure switch 6 is made through orifices 17 and 18 to further reduce surges generated across the orifice 5. Thus the differential pulsation filter moderates the air pressure surges in the air stream and provides a relatively constant level of pressure to the pressure switch which represents the average of the pressure drop generated across orifice 5 and allows for smooth and continuous operation of the air pump since the signal generated by the pressure switch is utilized by the integrator circuit to control the operation of the air pump.

Generally, a differential pressure switch is used that has a set point that is about the same as the pressure drop across the orifice and that is sensitive to a pressure drop change in the air stream of about 0.01-0.5 inches of water. The sensitivity of the switch or the amount of pressure required to activate the switch determines the number of signal changes fed to the integrator. A switch having a low level of sensitivity would feed fewer on-off changes of signal to the integrator than would a switch of high sensitivity. A switch with a fixed level of sensitivity or a switch with an adjustable level of sensitivity can be used.

As pointed out above, the flow rate of the air stream is determined by the by-pass valve, the size opening in the orifice and by the sensitivity of the pressure switch. When it is desired to operate under fixed conditions a non-adjustable orifice can be used with a fixed pressure switch. When it is desired to operate under variable conditions, an adjustable orifice or an adjustable pressure switch can be used or both the orifice and the pressure switch can be adjustable.

The integrator circuit takes the on-off signal generated by the pressure switch and formulates a slowly changing continuous signal therefrom which is fed into the amplifier circuit. The integrator circuit is biased at about +0.6 volts and the signal from the switch increases to about 1.2 volts when the pressure switch is activated and decreases to about +0.0 volts when the switch is deactivated. The integrator circuit produces a gradually decreasing output voltage which feeds into the amplifier when the pressure switch is closed and a gradually increasing voltage when the pressure switch is open. The circuit is constructed of conventional transistors, capacitors and resistors. An example of the circuit will be described hereinafter.

The amplifier circuit receives the signal generated by the integrator circuit and amplifies the signal so that the electric D.C. motor can be controlled at various speeds to insure a constant flow rate of the air stream through the dosimeter. The amplifier circuit amplifies the signal from the integrator to a maximum of about 96% of the total voltage of the power source. For example, for a 5 volt power source, the signal will be amplified to 4.8 volts. Generally, the amplifier has an impedance of greater than 10 ohms and up to 1 megohm. However, an amplifier with an impedance of less than 10 ohms can be used, e.g., 0.01-10 ohms impedance. The amplifier is constructed of conventional transistors, capacitors and resistors.

The power source usually is a battery of about 5-6 volts. Generally, two nickel cadmium batteries of 4 cells each are used. A direct current power source of rectified A.C. current can also be used.

One optional circuit that can be used in the dosimeter is a battery check circuit. The circuit uses a precision voltage detector which can be adjusted to the voltage of each cell and is set to be activated at the full charge voltage of the battery. A light emitting diode which is activated by a switch is usually used to indicate a full charge of the battery.

Another optional circuit that can be used in the dosimeter is a low air flow detector circuit which is connected to the integrator circuit and is activated when the voltage output of the integrator circuit is at higher than normal operational levels caused by an interruption of the air stream being pumped through the dosimeter. The low flow detector circuit comprises a bistable multivibrator circuit electrically connected to an indicator light such as a light emitting diode.

Another optional circuit that can be used in the dosimeter is a timer circuit. The timer can have both a timing feature to indicate the amount of running time and it can have a pre-set feature to stop the pump at the end of a pre-set time period.

There are two versions of the timing feature required to cover all the various sampling situations. The first is a timer that automatically rests itself to zero at the start of each testing period when the power switch is turned on. The second version is a timer that does not reset when the pump is turned off and on and keeps track of the total cumulative running time. This version of course requires a separate, manual reset switch to perform the resetting function.

Figure 3:
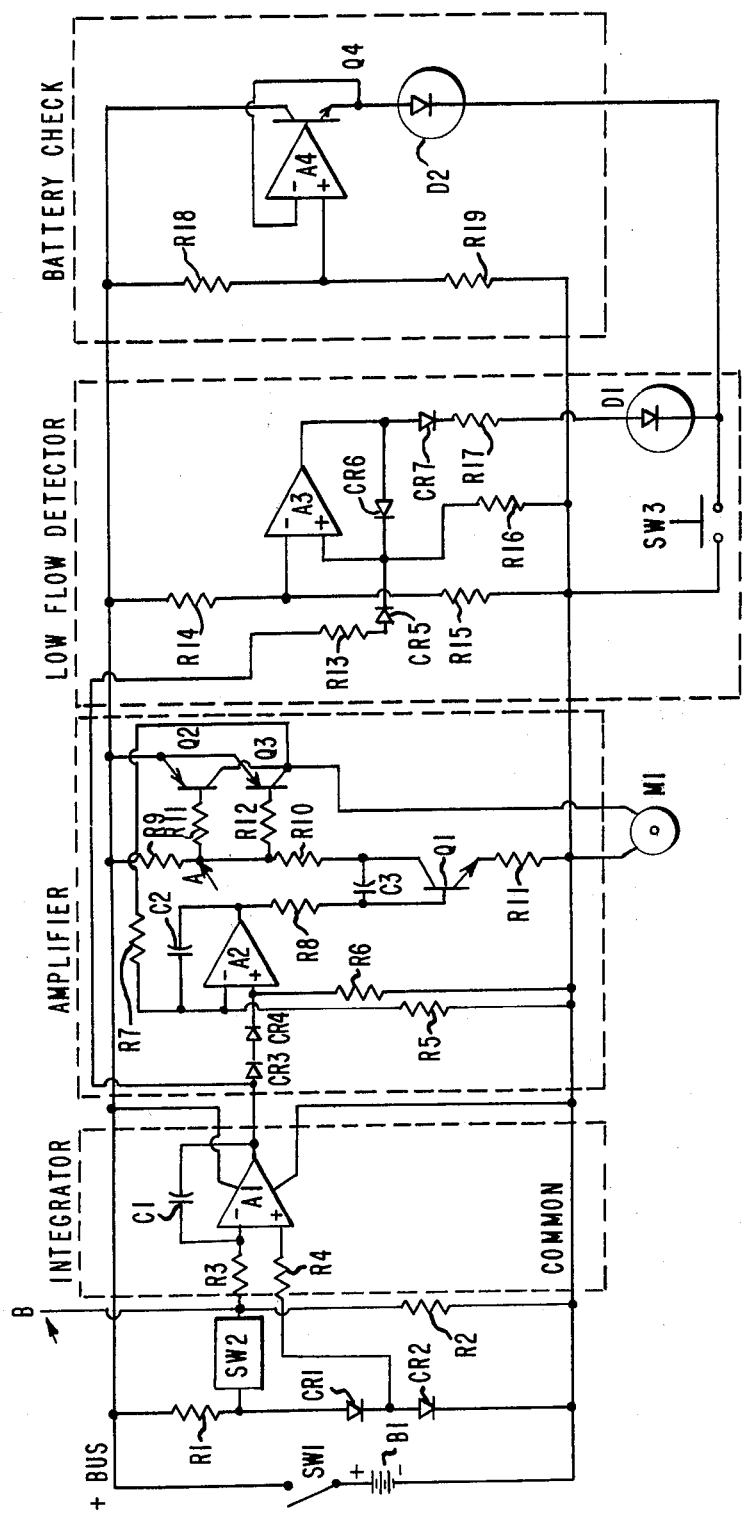
FIG. 3—is a schematic circuit diagram for one preferred embodiment of the dosimeter which contains a low air flow detector circuit and a battery check circuit.

FIG. 3 is a schematic diagram of the pump control system including a pressure switch driving an integrator circuit, an amplifier which drives the pump motor, a low air flow detector circuit and a battery charge indicator.

In FIG. 3, the battery B 1 which supplies power to the circuit has its negative (−) terminal connected to COMMON and its positive (+) terminal connected to power sitch SW 1. The other side of SW 1 is connected to the positive (+) BUS.

Amplifier A 1 (which may be operational amplifier such as one of the four amplifiers in a type LM 324 Quad Operational Amplifier) is connected in an integrating configuration with a feedback capacitor C 1 (typically 6.8 microfarads) connected from the out to the inverting (−) input of the amplifier A 1. The input resistor R 3 (typically 12 megohm) is connected to the inverting input of A 1. The values of R 3 and C 1 determine the integration rate and affect the response of the control circuit. The values are selected to give the best control with a particular pump and differential pulsation filter.

Resistor R 1 (typicaly 10 K ohms) is connected from the +BUS to one anode of diode, CR 1 (typically type IN 4148) and the cathode of CR 1 is connected to the anode of diode CR 2 (typically type IN 4148) which has the cathode connected to COMMON. This provides bias voltages of approximately 0.6 volt at the CR 2 anode and 1.2 volts at the CR 1 anode due to the forward voltage drops of the two diodes. The 0.6 volt point is connected to the non-inverting input (+) of the amplifier, A 1, to bias the +input at 0.6 volts above COMMON, through a resistor R 4 (typically 12 megohm) which minimizes amplifier offset voltage effects. A resistor R 2 (typically 22 K ohm) is connected from the input resistor R 3 (Point B) to COMMON or ground. This provides 0.0 volts to the input resistor when pressure switch SW 2 is open.

SW 2 typically is a pressure switch that operates at 3.0 inches of water pressure. The integrator produces a gradually decreasing voltage at the amplifier output when SW 2 is closed and a gradually increasing voltage when SW 2 is open. The voltage at the amplifier A 1 output is a motor speed signal which when amplified by an amplifier (described hereinafter) determines the pump motor speed. Connection from the +BUS and COMMON are made to A1 to provide power. These connection provide power for A 2, A 3 and A 4.

The motor speed signal is applied to amplifier A 2 (typically ¼ of a type LM 324 through series connected diodes CR 3 and CR 4 (typically IN 4143) to the non-inverting (+) input of A2. Load resistor R6 is connected from the input of A 2 to ground. The amplified signal from the output of A 2 is applied to the base of transistor Q 1 (typically an NPN type 2N2926) through resistor R 8 (typically 10 K ohm). The signal from the collector of Q 1 is applied to the base of parallel connected transistor Q 2 and Q 3 (typicaly PNP Type 2N5226) throught resistor R 10 (typically 100 ohm) connected to point A and through Resistors R 11 and R 12 (typically 100 ohm) connected from point "A" to the transistor bases. The output signal from the common collectors of Q 2 and Q 3 is connected to the pump motor M 1, a variable speed, direct current motor. The other side of M 1 is connected to COMMON.

The emitter of Q 1 is connected to COMMON through resistor R 11 (typically 220 ohm). Capacitor C 3, (typically 0.01 microfarad) is connected from base to collector Q 1 to reduce noise in the circuit. The emitter of Q 2 and Q 3 is connected to the +BUS. Point "A" is connected to the +BUS through resistor R 9 (typically a 1 K ohm). A feedback reistor R 7 (typically 47 K ohm) is connected from the collectors of Q 2 and Q 3 to the inverting (−) input of A 2 to provide negative feedback. The inverting input of A 2 is connected to COMMON through resistor R 5 (typically 2.2 K ohm).

Resistors R 5 and R 7 determine the overall voltage gain of the circuit from the output of A 1 to the voltage connected to the pump motor. These resistors may be adjusted to provide the optimum balance between fast control response and stable operation in pumps of various characteristics. Capacitor C 2 (typically 0.01 microfarad) is connected from the output of A 2 to the inverting input of A 2 to reduce circuit noise. This connection of A 2, Q 1, Q 2, Q 3 and their associated resistor and capacitors is one of many amplifier circuits suitable for amplifying the motor speed signal from A 1 but this circuit provides a wide voltage range to the motor, typically 0 to 4.8 volts, and provides a constant voltage output preferred in some pump configurations such as where very low motor speed for low flow is required.

The output signal from A 1 varies from about 0 to 1.5 volts during normal control but can increase gradually on up to a saturation level of approximately 3 volts (for a power supply voltage of 4.0 volts) when the pump cannot maintain the required air flow such as when the inlet tube is linked and the air flow is blocked. By detecting when the output of A 1 exceeds 2.5 volts, a low flow detector is provided. Thus, amplifier A 3 (typically ¼ of a LM 324) is connected at its inverting input to a trip voltage level. If a voltage of a greater magnitude than the trip voltage level is applied to the non-inverting (+) input of A 3, the output of A 3 will change from the normal level of zero to a high level of approximately 4.8 volts (with a volt power supply).

Resistor R 14 (typically 47 K ohm) is connected from the +BUS to resistor R 15 (typically 22 K ohm). The other side of R 15 is connected to COMMON. The junction between R 14 and R 15 is connected to the inverting (−) input of A 3.

Diode CR 6 (typically a type IN 4148) is connected from the A 3 output to the non-inverting input to keep the A 3 output high even if the original voltage signal is removed. Diode CR 7 typically a type 1 N 4148) resistor R 17 (typically 220 ohm); light emitting diode, D 1 (typically a HP 5082-4484); and a momentary test switch SW 3 are series connected from the output of A 3 to COMMON. When SW 3 is closed with the output of A 3 high, D 1 will light. Amplifier A 3 may be reset to the low output condition by opening switch SW 1 to remove power from the circuit. Resistor R 16 (typicaly 1.2 megohm) is connected from the non-inverting input of A 3 to COMMON to assure that A 3 does not inadvertantly go to the high output condition when power is first applied to the circuit. Resistor R 13 (typically a 41 K ohm) is connected from the output of A 1 to the anode of diode CR 5 (typically a type IN 4148) which is in turn connected to the non-inverting input of A 3 coupling the signal from A 1 into the flow detector circuit. The forward voltage drop of CR 5 helps prevent spurious signals from falsely tripping the low flow detector. In this configuration, the circuit normally requires 20 seconds after flow is interrupted until the circuit trips. This time can be decreased by increasing the ratio of R 14 to R 15.

A battery check circuit is built based on a special light emitting diode, D 2 (typically tupe HP 5082-4732 manufactured by the Hewlett-Packard Corporation) which lights at a specific level of applied voltage (typically 2.4 volts). Amplifier A 4 (typically ¼ of a type LM 324) has its output driving a transistor Q 4 (typically a 2 N 2926). The collector of Q 4 is connected to the inverting (−) input of A 4 providing a 1 X gain for signals applied to non-inverting input (+). The emitter of Q 4 is connected to the anode (or +input) of D 2 and the cathode of D 2 is connected to one side of switch SW 3. The other side of SW 3 is connected to COMMON. D 2 will light if SW 3 is closed and the output of A 4 is greater than a trigger voltage (typically 2.4 volts). Resistor R 18 (typically 100 K ohm) is connected from the +BUS to the non-inverting (+) input of A 4 and resistor R 19 (typically 100 K ohm) is connected from the (+) input of A 4 to COMMON. The ratio of R 18 and R 19 can be adjusted to present 2.4 volts to the non-inverting input of A 4 at the desired battery voltage check level, typically 5.15 volts for a battery constructed by connecting four nickel cadmium rechargeable cells in series.

In practical operation of the dosimeter, the dosimeter is placed in an area where workers are operating or is worn by a worker. Usually an 8 hour work shift is the time period the dosimeter is run. At the end of the shift, the circuit is tested to determine if the intake was blocked during the period by observing the light emitting diode (D 1 of FIG. 3) while pressing the momentary switch (SW 3 of FIG. 3). If the diode lights, blockage has taken place during the shift the filter is then removed from the dosimeter and sent to a laboratory for analysis and the results are recorded. If there is excessive exposure, workers can be withdrawn from the particular area and given another job.

I claim:

1. An improved dosimeter that has an electric motor, a power source, an exhaust port, a filter means in which particles or vapors present in an air stream being pumped through the dosimeter at a controlled constant flow rate are collected on the filter means;
    a variable drive pump having an inlet and an outlet, tubularly connected to the filter means and coupled to the electric motor, draws the air stream through the filter means;
    an orifice being positioned in a tube attached to the pump and to an exhaust port, wherein the air stream is pumped through the orifice and thereby creates an air pressure drop;
    means for reducing pulsations in the air stream;
    a differetial pressure switch positioned in a tube connected in effect parallel to the orifice is activated by a change in the air pressure drop of the air stream and creates a low voltage electrical input signal;

an integrator circuit electrically connected to a power source and to the pressure switch uses the low voltage input signal generated by the pressure switch and integrates this signal;

an amplifier circuit electrically connected to the power source and connected in series to the integrator circuit and to the electric motor which amplifies the signal generated by the integrator circuit and feeds the amplified signal to the electric motor thereby controlling the speed of the motor driving the pump in relationship to the signal generated by the pressure switch to maintain the air stream at a controlled constant flow rate; the improvement in use therewith comprises;

an adjustable by-pass valve connected in parallel with the variable drive pump whereby a fixed quantity of air from the outlet of the pump is recycled to the inlet of the pump allowing the pump to provide a constant low air flow rate of the air stream through the dosimeter.

2. The dosimeter of claim 1 in which the by-pass valve is an adjustable needle valve.

3. The dosimeter of claim 1 in which the by-pass valve is a valve having a fixed opening in the valve.

4. The dosimeter of claim 3 in which the orifice is an adjustable needle valve.

5. The dosimeter of claim 4 in which the pressure switch is activated by an air pressure drop of 3 inches of water and an air pressure drop change of 0.01 to 0.5 inches of water.

6. The dosimeter of claim 5 in which the integrator circuit is biased at about +0.6 volt and the signal from the integrator gradually increases to about +1.2 volts when the pressure switch is activated and gradually decreases to +0.6 volt when the switch is deactivated.

7. The dosimeter of claim 6 in which the amplifier circuit amplifies the signal from the integrator circuit to a maximum of about 96% of the total voltage of the power source and has an impedance of greater than 10 ohms.

8. The dosimeter of claim 7 which has electrically attached to the output of the integrator circuit thereto a low air flow detector circuit comprising a bistable multivibrator circuit electrically connected to an indicator light.

9. The dosimeter of claim 8 which has electrically connected to the power source which is a battery check circuit comprising a precision voltage detector adjusted to the full charge voltage of the battery.

10. The dosimeter of claim 9 in which the means for reducing pulsations in the air stream comprise a differential pulsation pressure filter positioned in a tube connected to the exhaust port and in parallel with the orifice.

11. The dosimeter of claim 10 in which the pump is a multicylinder piston pump.

12. The dosimeter of claim 10 in which the pump is a four cylinder diaphragm pump.

13. The dosimeter of claim 9 in which the means for reducing pulsations in the air stream comprise an air reservoir connected to the pump and to the orifice wherein the air reservoir retains excess air supplied by the pump and maintains a constant flow rate of the air stream.

14. The dosimeter of claim 13 in which the pump is a single cylinder diaphragm pump.

15. The dosimeter of claim 1 in which the adjustable by-pass valve is a valve having a fixed opening in the valve;

the pump is a diaphragm pump having four cylinders;

the orifice is an adjustable needle valve which causes an air pressure drop of about 3 inches of water;

the means for reducing pulsations in the air pressure stream comprise a differential pulsation pressure filter position in a tube connected to the exhaust port and in parallel with the orifice;

the pressure switch is activated by an air pressure drop change of about 0.1 to 0.5 inches of water;

the integrator circuit is biased about +0.6 volt and the signal from the circuit gradually increases to about +1.2 volts when the pressure switch is activated and gradually decreases to +0.6 volt when the pressure switch is deactivated;

the amplifier circuit amplifies the signal from the integrator circuit to a maximum of about 96% of the total voltage of the power source and has impedance less than 10 ohms;

the power source is a battery that has a maximum of 5.5 volts and has nickel cadmium cells; and has electrically connected thereto a low flow air detector circuit electrically attached to the output of the integrator circuit comprising a bistable multivibrator circuit electrically connected to an indicator light and a battery check circuit electrically connected to the power source which is a battery comprising a precision voltage detector adjusted to about 5.2 volts.

16. The dosimeter of claim 1 in which the adjustable by-pass valve is a valve having a fixed opening in the valve;

the pump is a diaphragm pump having one cylinder;

the means for reducing pulsations in the air stream comprise an air reservoir connected to the pump and to the orifice wherein the air reservoir retains excess air supplied by the pump and maintains a constant flow rate of the air stream;

the air pressure switch is activated by an air pressure drop change of about 0.1 to 0.5 inches of water;

the integrator circuit is biased about +0.6 volt and the signal from the circuit gradually increases to about +1.2 volts when the pressure switch is activated and gradually decreases to +0.6 volt when the pressure switch is deactivated;

the amplifier circuit amplifies the signal from the integrator circuit to a maximum of about 96% of the total voltage of the power source and has impedance less than 10 ohms;

the power source is a battery that has a maximum of 5.5 volts and has nickel cadmium cells; and has electrically connected thereto a low flow air detector circuit electrically attached to the output of the integrator circuit comprising a bistable multivibrator circuit electrically connected to an indicator light and a battery check circuit electrically connected to the power source which is a battery comprising a precision voltage detector adjusted to about 5.2 volts.

* * * * *